(12) United States Patent
Callister (10) Patent No.: US 8,313,915 B2
(45) Date of Patent: Nov. 20, 2012

(54) EARLY DETECTION OF CANINE LYME DISEASE BY SPECIFIC PEPTIDES AND ANTIBODIES

(75) Inventor: Steven M. Callister, Onalaska, WI (US)

(73) Assignee: Gundersen Lutheran Medical Foundation, Inc., La Crosse, WI (US)

( * ) Notice: Subject to any disclaimer, the term of this patent is extended or adjusted under 35 U.S.C. 154(b) by 118 days.

(21) Appl. No.: 12/690,663

(22) Filed: Jan. 20, 2010

(65) Prior Publication Data

US 2010/0184086 A1 Jul. 22, 2010

Related U.S. Application Data

(60) Provisional application No. 61/146,179, filed on Jan. 21, 2009.

(51) Int. Cl.
*G01N 33/53* (2006.01)

(52) U.S. Cl. ..... 435/7.1; 435/7.2; 424/184.1; 424/234.1

(58) Field of Classification Search ........................ None
See application file for complete search history.

(56) References Cited

U.S. PATENT DOCUMENTS

| | | | |
|---|---|---|---|
| 5,593,861 | A | 1/1997 | Maeda et al. |
| 5,726,010 | A | 3/1998 | Clark |
| 6,475,492 | B1 | 11/2002 | Phillipp et al. |
| 6,740,744 | B2 | 5/2004 | Norris et al. |
| 8,137,678 | B2 | 3/2012 | Callister et al. |

FOREIGN PATENT DOCUMENTS

| | | |
|---|---|---|
| EP | 0339695 | 11/1989 |
| GB | 2188638 | 10/1987 |
| WO | 8601533 | 3/1986 |
| WO | 9007861 | 7/1990 |

OTHER PUBLICATIONS

Lovrich et al 2007, Clinical and Vaccine Immunology ; 14 (5):635-637.*
Barbour et al., J. Inf. & Immun. 76, No. 8, (2008): 3374-3389.
Donahue et al., Am. J. Trop. Med. 36, No. 1, (1987): 92-96.
Greene et al., J. Clin. Micro. 26, No. 4, (1988): 648-653.
Zhang et al., Cell 89 (1997): 275-285.
Aguero-Rosenfeld et al., Clin. Micro. Reviews 18, No. 3, (2005): 484-509.
Levy et al, Veterinary Therapeutics 3, No. 3, (2002): 308-315.
Amit et al., Science 233, (1986): 747-753.
Queen et al., Proc. Natl. Acad. Sci. USA 86, (1989): 10029-10033.
Riechmann et al., Nature 332, (1988): 323-327.
Huse et al., Science 246, (1989): 1275-1281.
Carrillo and Lipman, Siam, J. Applied Math. 48, No. 5, (1988): 1073-1082.
Devereux et al., Nucl. Acids Res., 12, No. 1, (1984): 387-395.
LeFebvre et al., J. Clin. Microbiol., 27, No. 4, (1989): 636-639.
Jackson et al., J. Clin. Microbiol., 40, No. 6, (2002): 2070-2073.
Callister et al., J. Clin. Microbiol., 28, No. 2, (1990): 363-365.
Jobe et al., Clin. Diagn. Lab. Immunol.,10, No. 4, (2003): 573-578.
Rousselle et al., J. Infect. Dis., 178, (1998): 733-741.
Lovrich et al., Clin. Vacc. Immunol. 14, No. 5, (2007): 635-637.
Wieneke et al., J. Clin. Microbiol. 38, No. 1, (2000): 313-317.
LaFleur et al., Clin. Vacc. Immunol. 16, No. 2, (2009): 253-259.
Mark and Padlin, "Humanization of Monoclonal Antibodies," Chapter 4 in The Handbook of Experimental Pharmacology, vol. 113. The Pharmacology of Monoclonal Antibodies. New York: Springer-Verlag, 1994.
Wettendorff, M. et al. "Modulation of Antitumor Immunity by Anti-idiotypic Antibodies." in Idiotypic Network and Diseases, edited by J. Cerny and J. Hiernaux. J. Am. Soc. Microbiol. (1990): 203-229.
Lesk, A. M. , ed. Computational Molecular Biology. New York: Oxford University Press, 1998.
Smith, D. W., ed. Biocomputing: Informatics and Genome Projects. New York: Academic Press, 1993.
Griffin, A. M., and H. G. Griffin, eds. Computer Analysis of Sequence Data, Part 1. Totowa, N. J.: Humana Press, 1994.
von Heijne, G. Sequence Analysis in Molecular Biology. New York: Academic Press, 1987.
Gribskov, M., and J. Devereux., eds. Sequence Analysis Primer. New York: M. Stockton Press, 1991.
Harlow, E., and D. Lane., eds. Antibodies: A Laboratory Manual. New York: Cold Spring Harbor Laboratory Press, 1988.

* cited by examiner

*Primary Examiner* — Padma Baskar
(74) *Attorney, Agent, or Firm* — Pierce Atwood LLP; Kevin M. Farrell; David J. Wilson (57) ABSTRACT

The present invention relates, in one aspect, to the detection of Lyme disease in canines by detecting the peptide or antibodies to an infection specific peptide after challenge with *B. burgdorferi*. The 20 kDa peptide is not detectable in human sera samples after challenge or infection with *B. burgdorferi* and, as such, appears to be specific for canines and suitable for the consistent detection of Lyme disease in canines at time points earlier that possible with prior art methods.

8 Claims, 2 Drawing Sheets

EARLY DETECTION OF CANINE LYME DISEASE BY SPECIFIC PEPTIDES AND ANTIBODIES

BACKGROUND

The bacterium *Borrelia burgdorferi* (sensu lato) is the causative agent of Lyme borreliosis, i.e., Lyme disease. This illness is caused by transmission of the spirochetes by the bite of various species of Ixodes ticks. The main reservoir of the infection in the United States is the white footed mouse, *Peromyscus leucopus*, and the infection can be transmitted to many mammalian species including dogs, cats and man [J. G. Donahue, et al., Am. J. Trop. Med. Hyg., 36:92-96 (1987); R. T. Green, et al, J. Clin. Micro., 26:648-653 (1988)]. In addition, the disease may persist for years despite an active immune response and such persistence is postulated to be the result, at least in part, of antigenic variation in the bacterial proteins [J. R. Zhang, et al., Cell, 89:275-285 (1997)].

There have been numerous publications relating to proteins and polypeptides of *Borrelia burgdorferi* and their potential use as diagnostic or pharmaceutical agents, but the vast majority have focused on the humoral immune response during human infection. The result has been widespread availability of accurate serodiagnostic tests for confirming the illness in humans [See, for example, Aguero-Rosenfeld, et al., Diagnosis of Lyme Borreliosis, Clinical Microbiology Reviews, July 2005, p. 484-509 and references contained therein]. However, the humoral immune responses during canine Lyme disease have not to date been studied extensively. Rather, serodiagnostic tests developed for human use have been used interchangeably in canines and the result has been considerable confusion caused primarily by inaccuracy of test results. Researchers [Lovrich, S. D., et al., Clinical and Vaccine Immunology, 14:635-637, 2007] recently provided explanation for the confusion by confirming significant differences in the specificities of the antibody responses that occur during human or canine Lyme disease. In fact, only one test developed originally for confirming human Lyme disease, detecting antibodies to the C6 peptide, has been proven useful for confirming the illness in dogs [Levy, S A, et al., Veterinary Therapeutics, 3:308-315, 2002] and the procedure is now considered the gold standard. However, response to C6 is often not detectable until several weeks or months after infection. Therefore, there exists a clear need in the art for a simple, sensitive and specific diagnostic composition and method, especially for early detection of Lyme disease in canines.

SUMMARY OF THE INVENTION

The present invention relates to methods for the detection of canine Lyme disease with greater sensitivity over prior art methods. The methods and compositions of the present invention are specific for canine Lyme disease and are effective in the detection of canine Lyme disease with greater sensitivity than prior art methods by, for example, the detection of antibodies specific for a 20 kDa peptide that is a specific indicator for infection of canines by *Borrelia burgdorferi*. Antibodies specific for this 20 kDa peptide have not been detected in *B. burgdorferi* challenged humans but are present in challenged canines and may be present in other non-human animals [Lovrich, S. D., et al., Clinical and Vaccine Immunology, 14:635-637, 2007, which is incorporated herein]. One of skill in the art would be able to determine the presence of the anti-p20 peptide antibodies in other non-human animals other than canines without undue experimentation based on the teachings of the present specification. As used herein, the p20 peptide is also referred to as the 20 kDa peptide, the p20 polypeptide, the p20 antigen and the p20 protein. The p20 peptide is an approximately 20 kDa *B. burgdorferi* peptide that is recognized by antibodies in sera from dogs, but not humans, challenged with *B. burgdorferi*. As is understood in the art, the p20 peptide may also comprise sugars, lipids or other moieties typically associated with peptides and proteins in addition to amino acids. Additionally, the p20 peptide may be posttranslationally modified and any p20 epitope/antigen may include such modifications. Also, as defined herein, an "isolated" peptide, polypeptide, protein, antigen or epitope includes a peptide separated from a mixture of proteins using standard techniques including gel electrophoresis or chromatography. Further, the term "animal," as defined herein, is any non-human animal and preferably a mammal.

The current "gold standard" for the detection of infection of Lyme disease in canines is the detection of antibodies to the C6 peptide. See, U.S. Pat. No. 6,475,492 to Phillipp, et al., which is incorporated herein by reference. However, this prior art method has low sensitivity in the early stages of infection in canines, as compared to the present invention. An earlier detection of Lyme infection is advantageous because it allows the veterinarian to commence treatment of the disease at an earlier stage, which will shorten the length of time symptoms are experienced by the infected animal and increases the likelihood of treatment success.

A response to the 20 kDa peptide of the present invention, e.g., antibodies thereto, is detectable in about 71% of infected dogs one month after infection and in about 88% of infected dogs three months after infection. In comparison, response to the C6 peptide is detectable in only about 13% of infected dogs one month after infection and only about 67% of infected dogs three months after infection. Thus, the present invention makes the detection of Lyme infection in canines possible at a much earlier time point and in a greater number of dogs than the previous "gold standard" of detection of infection by assaying for antibodies to the C6 peptide.

The present invention relates to the detection of Lyme disease by, for example, detecting antibodies to an approximately 20 kDa (kilo Dalton) infection-specific peptide in canines after challenge with *B. burgdorferi*. Antibodies specific for the 20 kDa peptide were not detectable in human serum samples by Western blot after challenge or infection with *B. burgdorferi* and, as such, the antibodies may be specific for canines or non-human animals.

Antibodies against the 20 kDa peptide of the present invention are also not detectable after vaccination of canines thereby making it useful for the detection of infection even in previously vaccinated dogs. See, Exemplification and Table 4, below. It is understood in the art that not all vaccines are 100% effective and vaccinated dogs may become infected with Lyme disease. Therefore, the present invention is suitable for the detection of disease in vaccinated canines. The present invention therefore allows for vaccinated animals to be distinguished from infected animals. This is important, inter alia, because animals that are vaccinated and not infected should not be unnecessarily treated for Lyme disease.

BRIEF DESCRIPTION OF THE FIGURES

FIGS. 1 (A & B) shows an example of IgM (A) and IgG (B) antibodies detected in dogs by Western blot using immune sera collected one month after infection with *B. burgdorferi* by challenge with infected ticks.

FIGS. 2 (A & B) shows an example of IgG antibodies in dogs detected by Western blot in immune sera collected three months post-*B. burgdorferi* infection by tick transmission after removal of OspC-specific antibodies (lane B). Lane A is normal dog serum. Note: Antibodies detecting the 20 kDa protein are not affected.

DETAILED DESCRIPTION OF THE INVENTION

The present invention satisfies an existing need in the art by providing methods and compositions (e.g., kits) which permit rapid and accurate detection of canine Lyme disease. In this regard, the present invention relates in one aspect to the early detection of infection of canines with *B. burgdorferi*. More specifically, as shown in the Exemplification section, which follows, methods of the present invention are capable of detection of *B. burgdorferi* infection in as little as one month after infection. In another aspect, the present invention relates to the detection of the presence or absence of *B. burgdorferi* infection even in dogs that have been vaccinated. In yet another aspect, the present invention provides a method for distinguishing animals infected with *Borrelia* from animals that have been vaccinated against (but not infected with) *Borrelia*. Further, the present invention relates to kits useful in connection with the methods disclosed herein.

In a currently preferred embodiment, the invention provides peptide-based assays, e.g., ELISAs, which in terms of simplicity, specificity and sensitivity, are superior to current serologic diagnostic methods for canine Lyme disease. Further, the assays of the invention are also useful in serum samples that contain anti-p20 antibodies, permitting diagnosis of Lyme disease in subjects that have been exposed to the causative agent of Lyme disease. The present invention can detect the presence or absence of exposure or infection by *B. burgdorferi* even in dogs that have been vaccinated against *Borrelia*. As noted above, no vaccine is 100% effective and even vaccinated dogs may become infected.

As shown in the Exemplification section below, the present invention is superior to the prior art compositions and methods for the detection of Lyme disease. The compositions and methods of the present invention permit the detection of Lyme disease in canines at a much earlier time point than the prior art method of detecting antibodies to the C6 peptide making the compositions and methods of the present invention superior to those of the prior art. Lyme disease responds best to treatment the earlier treatment is started. Therefore, earlier detection permits earlier treatment of the animal and, therefore, better chances for symptom remittal or a cure.

The methods and compositions (e.g., kits) of the invention utilize a peptide referred to herein as p20 and/or antibodies directed towards the p20 peptide. The p20 peptide is characterized by the generation of antibodies in canines that are infected with *B. burgdorferi*. The antibodies are specific to and recognize the p20 peptide. Antibodies against the p20 peptide were not found in human Lyme disease serum by Western blot. Antibodies specific for the p20 peptide do not cross react with OspC, a slightly larger *B. burgdorferi* coat protein. In fact, in Lyme disease canines positive for antibodies reactive with OspC are only rarely detected. The p20 peptide is an isolated *Borrelia burgdorferi* polypeptide and has an apparent molecular weight of about 20 kD. The p20 peptide (and/or the antibodies directed toward p20) provides the specificity for canine Lyme disease (and, potentially, other non-human animals) which is an advantage of the invention. Also contemplated in the present application are proteins containing this peptide (e.g., fusion proteins), as well as antibodies directed thereto for use in diagnostic, therapeutic and prophylactic compositions and methods for the treatment or prevention of Lyme disease. The invention provides advantages over the use of other *Borrelia* proteins and antibodies in known compositions and methods for this purpose.

I. Diagnostic Methods and Assays

The present invention provides reliable and accurate methods of diagnosing canine Lyme disease. These diagnostic methods are useful for diagnosing canines exhibiting the clinical symptoms of, or suspected of having, Lyme disease. The p20 peptides, proteins and antibodies of the invention are particularly well suited for use in the diagnostic methods and compositions of the invention and, for convenience, reference will be made to p20 throughout this and the following section.

One aspect the invention is directed to an immunological method, devices and kits for detecting the presence of antibodies specific for the 20 kDa protein in a biological sample. The method may include controls, calibrators or standards comprising one or more antibodies specific for the 20 kDa protein. In particular, the method may be accomplished using immunoassay techniques well known to those of skill in the art, including, but not limited to, using microplates and lateral flow devices.

Detection of 20 kDa protein/antibody complexes may be achieved through a variety of techniques well know in the art, such as, for example, turbidimetry, enzymatic labeling, radiolabeling, luminescence or fluorescence. Immunoassay methodologies are known by those of ordinary skill in the art and are appreciated to include, but not limited to, radioimmunoassay (RIA), enzyme immunoassays (EIA), fluorescence polarization immunoassays (FPIA), microparticle enzyme immunoassays (MEIA) and chemiluminescent magnetic immunoassays (CMIA). In RIA, an antibody or antigen is labeled with radioactivity and used in a competitive or non-competitive format. In EIA, an antibody or antigen is labeled with an enzyme that converts a substrate to a product with a resulting signal that is measured, such as a change in color. In FPIA, an antigen is labeled with fluorescent label and competes with unlabeled antigen from the specimen. The amount of analyte measured is inversely proportional to the amount of signal measured. In MEIA, a solid phase microparticle is coated with antibodies against an antigen of interest and is used to capture the analyte. The antibody for detection is labeled with an enzyme as in the EIA method. The concentration of analyte measured is proportional to the amount of signal measured. In CMIA, a chemiluminescent label is conjugated to the antibody or antigen, and produces light when combined with its substrate. CMIA can be configured in a competitive or noncompetitive format, and yields results that are inversely or directly proportional to the amount of analyte present, respectively.

The use of reagent-impregnated test strips in specific binding assays is also well-known. In such procedures, a test sample is applied to one portion of the test strip and is allowed to migrate or wick through the strip material. Thus, the analyte to be detected or measured passes through or along the material, possibly with the aid of an eluting solvent which can be the test sample itself or a separately added solution. The analyte migrates into a capture or detection zone on the test strip, wherein a complementary binding member to the analyte is immobilized. The extent to which the analyte becomes bound in the detection zone can be determined with the aid of the conjugate which can also be incorporated in the test strip or which can be applied separately. In one embodiment, 20 kDa protein is immobilized on a solid support at a distinct location. Following addition of the sample, detection of 20 kDa protein/antibody complexes on the solid support can be by any means known in the art. For example, U.S. Pat. No.

5,726,010, which is incorporated herein by reference in its entirety, describes an example of a lateral flow device, the SNAP® immunoassay device (IDEXX Laboratories), useful in the present invention.

Other detection technologies employ magnetic particles or microbeads: for example, superparamagnetic iron oxide impregnated polymer beads. These beads are associated with, for example, a specific binding partner for the analyte. The beads bind with the target analytes in the sample being tested and are then typically isolated or separated out of solution magnetically. Once isolation has occurred, other testing may be conducted, including observing particular images or labels, whether directly optically or by means of a camera.

In one embodiment of the present invention, the diagnostic method involves detecting the presence of naturally occurring *B. burgdorferi* antibodies which are produced by the infected dog's immune system in its biological fluids and which are capable of binding to the antigens of this invention. This method comprises the steps of incubating a p20 peptide or protein of this invention with a sample of biological fluids from the canine. Antibodies present in the fluids as a result of *B. burgdorferi* infection will form an antibody-antigen complex with the antigen. Subsequently the reaction mixture is analyzed to determine the presence or absence of these antigen-antibody complexes. In some embodiments, the step of analyzing the reaction mixture comprises contacting the reaction mixture with a labeled specific binding partner for the antibody.

In another embodiment of the method, the p20 peptide or protein, or a mixture of the peptides and proteins of the invention is electro- or dot-blotted onto nitrocellulose paper (or any other suitable membrane known in the art, such as for example PVDF). Subsequently, the biological fluid (e.g., serum or plasma) is incubated with the blotted antigen and antibody in the biological fluid is allowed to bind to the antigen(s). The bound antibody is then detected by standard immunoenzymatic methods.

In another embodiment of the method, latex beads (or any other type of particle or micro-particle known in the art) are conjugated to the antigen(s) of this invention. Subsequently, the biological fluid is incubated with the bead/protein conjugate, thereby forming a reaction mixture. The reaction mixture is then analyzed to determine the presence of the antibodies.

In another embodiment, the diagnostic method of the invention involves detecting the presence of the naturally occurring p20 antigen(s) itself in its association with the *B. burgdorferi* pathogen in the biological fluids of an animal infected by the pathogen. This method includes the steps of incubating an antibody of this invention (e.g., produced by administering to a suitable animal an antigen of this invention), preferably conventionally labeled for detection, with a sample of biological fluids from an animal to be diagnosed. In the presence of *B. burgdorferi* infection of the animal patient, an antigen-antibody complex is formed (specific binding occurs). Subsequently, excess labeled antibody is optionally removed, and the reaction mixture is analyzed to determine the presence or absence of the antigen-antibody complex and the amount of label associated therewith.

Assays employing a protein antigen of the invention can be heterogeneous (i.e., requiring a separation step) or homogenous. If the assay is heterogeneous a variety of separation means can be employed including centrifugation, filtration, chromatography or magnetism.

One preferred assay for the screening of blood products or other physiological or biological fluids is an enzyme linked immunosorbant assay, i.e., an ELISA. Typically in an ELISA, the isolated antigen(s) of the invention is adsorbed to the surface of a microtiter well directly or through a capture matrix (i.e., antibody). Residual protein-binding sites on the surface are then blocked with an appropriate agent, such as bovine serum albumin (BSA), heat-inactivated normal goat serum (NGS), or BLOTTO (a buffered solution of nonfat dry milk which also contains a preservative, salts, and an antifoaming agent). The well is then incubated with a biological sample suspected of containing specific anti-*B. burgdorferi* antibody. The sample can be applied neat or, more often, it can be diluted, usually in a buffered solution which contains a small amount (0.1-5.0% by weight) of protein such as BSA, NGS or BLOTTO. After incubating for a sufficient length of time to allow specific binding to occur, the well is washed to remove unbound protein and then incubated with labeled anti-canine immunoglobulin ($\alpha$-canine-Ig) or other suitable antibody. The label can be chosen from a variety of enzymes including horseradish peroxidase (HRP), $\beta$-galactosidase, alkaline phosphatase and glucose oxidase, as described above. Sufficient time is again allowed for specific binding to occur. The well is washed again to remove unbound conjugate and the substrate for the enzyme is added. Color is allowed to develop and the optical density of the contents of the well is determined visually or instrumentally.

Further, MAbs or other antibodies of this invention which are capable of binding to the antigen(s) can be bound to ELISA plates. In another diagnostic method, the biological fluid is incubated on the antibody-bound plate and washed. Detection of any antigen-antibody complex and qualitative measurement of the labeled MAb is performed conventionally, as described above.

Methods of the invention can be accomplished using, for example, immunoassay techniques well known to those of skill in the art, including, but not limited to, using microplates and lateral flow devices. In one embodiment, one or more *Borrelia burgdorferi* antigens are immobilized on a solid support at a distinct location. Detection of antigen-antibody complexes on the solid support can be by any means known in the art. For example, U.S. Pat. No. 5,726,010, which is incorporated herein by reference in its entirety, describes an example of a lateral flow device useful in the present invention. The device of the invention can be used to detect one or more antibodies to *Borrelia burgdorferi* antigens.

Other useful assay formats include the filter cup and dipstick. In the former assay an antibody of this invention is fixed to a sintered glass filter to the opening of a small cap. The biological fluid or sample (5 ml) is worked through the filter. If the antigen is present (i.e., *B. burgdorferi* infection), it will bind to the filter which is then visualized through a second antibody/detector. The dipstick assay involves fixing an antigen or antibody to a filter that is then dipped in the biological fluid, dried and screened with a detector molecule.

It should be understood by one of skill in the art that any number of conventional protein assay formats, particularly immunoassay formats, may be designed to utilize the isolated antigens and antibodies of this invention for the detection of *B. burgdorferi* infection in animals. This invention is thus not limited by the selection of the particular assay format and is believed to encompass assay formats which are known to those of skill in the art.

II. Diagnostic Kits

For convenience, reagents for ELISA or other assays according to this invention may be provided in the form of kits. Such kits are useful for diagnosing infection with *B. burgdorferi* in an animal sample. Such a diagnostic kit contains an antigen of this invention and/or at least one antibody capable of binding an antigen of this invention. Such kits would also contain suitable instructions for use.

These kits can include microtiter plates to which the p20 peptides, proteins or antibodies of the invention have been pre-adsorbed. Also included may be various diluents and buffers, labeled conjugates for the detection of specifically bound antigens or antibodies and other signal-generating reagents such as enzyme substrates, cofactors and chromogens. Other components of these kits can easily be determined by one of skill in the art. Such components may include polyclonal or monoclonal capture antibodies, antigen of this invention or a cocktail of two or more of the antibodies (i.e., to different epitopes of the antigen), purified or semi-purified extracts of these antigens as standards, MAb detector antibodies, a secondary antibody with indicator molecule conjugated thereto, an ELISA plate prepared for absorption, indicator charts for colorimetric comparisons, disposable gloves, decontamination instructions, applicator sticks or containers, a sample preparator cup and use instructions. Such kits provide a convenient, efficient way for a clinical laboratory to diagnose B. burgdorferi infection.

III. Antibodies

The present invention also provides antibodies capable of recognizing and binding the p20 peptides of this invention, including antibodies derived from mixtures of such antigens or fragments thereof. These antibodies are useful in diagnosis of canine Lyme disease and in therapeutic compositions for treating dogs that test positive for or, prior to testing, exhibit symptoms of Lyme disease. The antibodies are useful in diagnosis alone (e.g., those antibodies raised using p20 peptides and proteins) or in combination with antibodies to other antigens of this invention as well as antibodies to other known B. burgdorferi antigens. These antibodies are useful, inter alia, in passive vaccine compositions.

The term "antibody," as used herein, generally refers to a glycoprotein produced by B lymphocyte cells in response to exposure to an antigen and binds specifically to that antigen. The term "antibody" is used in its broadest sense and specifically covers monoclonal antibodies (including full length monoclonal antibodies), polyclonal antibodies, multispecific antibodies (e.g., bispecific antibodies) and antibody fragments so long as they exhibit the desired biological activity.

As used herein, the term "antibody" also includes any protein or peptide containing molecule that comprises at least a portion of an immunoglobulin molecule, such as, but not limited to, one complementarity determining region (CDR) of a heavy chain or light chain constant region, a framework region, or any portion thereof.

The term "antibody fragment," as used herein, refers to a portion of a full length antibody, generally the antigen binding or variable domain thereof. Specifically, for example, antibody fragments may include Fab, Fab', F(ab')2, and Fv fragments; diabodies; linear antibodies; single-chain antibody molecules; and multispecific antibodies from antibody fragments.

The antibodies of this invention are generated by conventional means utilizing the isolated, recombinant or modified antigens of this invention or mixtures of such antigens or antigenic fragments. For example, polyclonal antibodies are generated by conventionally stimulating the immune system of a selected animal with the isolated antigen or mixture of antigenic proteins or peptides of this invention allowing the immune system to produce natural antibodies thereto and collecting these antibodies from the animal's blood or other biological fluid. Polyclonal antibodies can be isolated from infected animals.

Monoclonal antibodies (MAbs) directed against a p20 peptide or protein (or fragment thereof) of the present invention may also be generated. Hybridoma cell lines expressing desirable MAbs are generated by well-known conventional techniques, e.g., Kohler and Milstein and the many known modifications thereof. Similarly desirable high titer antibodies are generated by applying known recombinant techniques to the monoclonal or polyclonal antibodies developed to these antigens [see, e.g., PCT Patent Application No. PCT/GB85/00392; British Patent Application Publication No. GB2188638A; Amit, et al., Science, 233:747-753 (1986); Queen, et al., Proc. Nat'l. Acad. Sci. USA, 86:10029-10033 (1989); PCT Patent Application No. PCT/WO9007861; and Riechmann, et al., Nature, 332:323-327 (1988); Huse, et al., Science, 246:1275-1281 (1988a)].

Given the disclosure contained herein, one of skill in the art may generate chimeric, canine-ized or fully canine antibodies directed against a p20 peptide or protein of the invention by resort to known techniques by manipulating the complementarity-determining regions of canine antibodies to the antigen of this invention. See, e.g., E. Mark and Padlin, "Humanization of Monoclonal Antibodies", Chapter 4, The Handbook of Experimental Pharmacology, Vol. 113, The Pharmacology of Monoclonal Antibodies, Springer-Verlag (June, 1994), the techniques of which can also be used with modifications in the canine-ization of antibodies. See also U.S. Pat. No. 5,593,861, which is incorporated herein by reference. One of skill in the art will recognize that these or similar techniques will work to produce canine-ized or full canine antibodies.

Alternatively, the antigens may be assembled as multi-antigenic complexes [see, e.g., European Patent Application 0339695, published Nov. 2, 1989] or as simple mixtures of antigenic proteins/peptides and employed to elicit high titer antibodies capable of binding the selected antigen(s) as it appears in the biological fluids of an infected canine.

Further contemplated by the present invention are anti-idiotype antibodies (Ab2) and anti-anti-idiotype antibodies (Ab3). Ab2 are specific for the target to which anti-p20 antibodies (Ab1) of the invention bind and Ab3 are similar to Ab1 in their binding specificities and biological activities [see, e.g., M. Wettendorff, et al., "Modulation of anti-tumor immunity by anti-idiotypic antibodies" In Idiotypic Network and Diseases, ed. by J. Cerny and J. Hiernaux J, Am. Soc. Microbiol, Washington D.C.: pp. 203-229, (1990)]. These anti-idiotype and anti-anti-idiotype antibodies are produced using techniques well known to those of skill in the art. Such anti-idiotype antibodies (Ab2) can bear the internal image of the antigens and are thus useful for the same purposes as the p20 peptides and proteins of the invention.

In general, polyclonal antisera, monoclonal antibodies and other antibodies which bind to the selected antigen (Ab1) are useful to identify epitopes of p20 and to separate these peptides and proteins from contaminants in tissue (e.g., in chromatographic columns and the like) and in general as research tools and as starting materials essential for the development of other types of antibodies described above. Anti-idiotype antibodies (Ab2) are useful for binding the same target and thus may be used in place of the original antigen.

For use in diagnostic assays, the antibodies may optionally be associated with conventional labels which are capable, alone or in concert with other compositions or compounds, of providing a detectable signal. Where more than one antibody is employed in a diagnostic method, the labels are desirably interactive to produce a detectable signal. The label is detectable visually, e.g., colorimetrically, or by other known methods. A variety of enzyme systems have been described in the art which will operate to reveal a colorimetric signal in an assay. As one example, glucose oxidase (which uses glucose as a substrate) releases peroxide as a product. Peroxidase, which reacts with peroxide and a hydrogen donor such as tetramethyl benzidine (TMB), produces an oxidized TMB that is seen as a blue color. Other examples include horseradish peroxidase (HRP) or alkaline phosphatase (AP), and hexokinase in conjunction with glucose-6-phosphate dehydrogenase which reacts with ATP, glucose, and NAD+ to yield, among other products, NADH that is detected as increased absorbance at 340 nm wavelength. Other label systems that may be utilized in the methods of this invention are detectable by other means, e.g., colored latex microparticles [Bangs Laboratories, Ind.] in which a dye is embedded may be used in place of enzymes to form conjugates with the antibodies and provide a visual signal indicative of the presence of the resulting complex in applicable assays. Still other labels include fluorescent compounds, radioactive compounds or elements. Detectable labels for attachment to antibodies useful in diagnostic assays of this invention may be easily selected from among numerous compositions known and readily available to one skilled in the art of diagnostic assays. The methods and antibodies of this invention are not limited by the particular detectable label or label system employed. Suitably, these detectable systems may also be utilized in connection with diagnostic reagents composed of the peptides, proteins, and antibodies of the invention.

The terms "specifically bind(s)" or "specific for" means that an antigen of the present invention recognizes and binds to a first antigen, e.g., a *Borrelia burgdorferi* polypeptide, with greater affinity than to other non-specific molecules. A non-specific molecule is an antigen that shares no common epitope with the first antigen. For example, an antibody raised against a first antigen (e.g., a polypeptide) to which it binds more efficiently than to a non-specific antigen can be described as specifically binding to the first antigen. Specific binding can be tested using, for example, an enzyme-linked immunosorbant assay (ELISA), a radioimmunoassay (RIA) or a western blot assay using methodology well known in the art.

IV. Vaccine Compositions

The present invention contemplates a vaccine composition containing a p20 protein or peptide of the invention or fragments and mixtures thereof and a pharmaceutically acceptable carrier or diluent. Combinations of the antigen(s) of this invention with other antigens of *B. burgdorferi*, such as the OspA and OspB proteins, BmpA, B, C or D proteins or fragments and mixtures thereof are also encompassed by this invention.

Exemplary carriers are as described above for therapeutic compositions. Optionally, the vaccine composition may further contain adjuvants, preservatives, chemical stabilizers or other antigenic proteins. Typically, stabilizers, adjuvants and preservatives are optimized to determine the best formulation for efficacy in the target animal. Suitable exemplary preservatives include chlorobutanol, potassium sorbate, sorbic acid, sulfur dioxide, propyl gallade, paraben(s), ethyl vanillin, glycerin, phenol and parachlorophenol.

One or more of the above described vaccine components may be admixed or adsorbed with a conventional adjuvant. The adjuvant is used to attract leukocytes or enhance an immune response. Such adjuvants include, among others, Ribi, mineral oil and water, aluminum hydroxide, Amphigen, Avridine, L121/squalene, D-lactide-polylactide/glycoside, pluraonic plyois, muramyl dipeptide, killed *Bordetella* and saponins, such as Quil A. In addition, a vaccine composition of the invention may further comprise other, non-*B. burgdorferi* antigens, including, *Bordertella bronchiseptica*, canine parvovirus, canine distemper, rabies, *Leptosporidia*, canine coronavirus and canine adenovirus. Other vaccinal antigens originating from other species may also be included in these compositions, e.g., feline coronavirus, etc.

The invention thus also encompasses a prophylactic method entailing administering to an animal an effective amount of such a composition. The vaccine compositions of the invention are administered in an "effective amount," that is, an amount of antigen that is effective in a route of administration to provide a vaccinal benefit, i.e., protective immunity. Suitable amounts of the antigen can be determined by one of skill in the art based upon the level of immune response desired. In general, however, a protein-based vaccine composition contains between 1 ng to 1000 mg antigen, and more preferably, 0.05 mg to 1 mg per L of antigen. Generally, a DNA-based vaccine contains a nucleic acid sequence encoding a peptide or protein antigen of the invention optionally under the control of regulatory sequences. Where the antigen-encoding DNA is carried in a vector, e.g., a viral vector, a dose may be in the range of $1\times10^{-3}$ pfu to $1\times10^{12}$ pfu.

Other suitable doses of the vaccine composition of the invention can be readily determined by one of skill in the art. Generally, a suitable dose is between 0.1 to 5 ml of the vaccine composition. In general, the vaccine may be administered once on a seasonal basis. Each tick season, usually in the spring, a booster should be administered. The vaccine may be administered by any suitable route. However, parenteral administration, particularly intramuscular, and subcutaneous, is the preferred route. Also preferred is the oral route of administration. Routes of administration may be combined, if desired, or adjusted. Further, depending upon the subject being treated, i.e., its weight, age and general health, the dosage can also be determined readily by one of skill in the art.

V. The p20 Peptide

The p20 peptide antigen may be isolated or purified in a form substantially free from other proteinaceous and non-proteinaceous material such as, for example, components of the microorganism, the tick vector or the sample from the infected animal. In this regard, the terms "purified" and "isolated" (and equivalent terms) in regard to the p20 peptide of the present invention or antibodies to the p20 peptide of the present invention means that at least 25%, 50%, 75%, 90%, 95% or 99% of the non-aqueous components of a sample is comprised of the p20 peptide. The antigens may be isolated from the spirochete and further purified using any of a variety of conventional methods including: liquid chromatography such as normal or reversed phase HPLC, FPLC and the like; affinity chromatography (such as with inorganic ligands or monoclonal antibodies); size exclusion chromatography; immobilized metal chelate chromatography; gel electrophoresis, and the like. One of skill in the art may select the most appropriate isolation and purification techniques without departing from the scope of this invention.

The term "apparent molecular weight" (measured herein in kilodaltons: kDa) as used herein is intended to mean the molecular weight as determined by sodium dodecyl sulphate-polyacrylamide gel electrophoreisis (e.g., 4-20% SDS-PAGE gel) using molecular weight markers [Sigma, St Louis, Mo., e.g., cat. nos. S8445 or M3913, or equivalent].

As known in the art, "homology" or "identity" means the degree of sequence relatedness between two peptides or two nucleotide sequences as determined by the identity of the match between two lengths of such sequences. Both identity and homology can be readily calculated by methods extant in the prior art [See, e.g., Computational Molecular Biology, Lesk, A. M. ed., Oxford University Press, New York, (1988);

Biocomputing: Informatics And Genome Projects, Smith, D. W. ed., Academic Press, New York, (1993); Computer Analysis Of Sequence Data, Part I, Griffin, A. M., and Griffin, H. G., eds. Humana Press, New Jersey, (1994); Sequence Analysis In Molecular Biology, von Heinje, G., Academic Press, (1987); and Sequence Analysis Primer, Gribskov, M. and Devereux, J., eds. M Stockton Press, New York (1991)]. While there exist a number of methods to measure identity and homology between amino acid or nucleotide sequences, the terms "identity," "similarity" and "homology" are well known to skilled artisans [H. Carillo and D. Lipton, SIAM J. Applied Math., 48:1073 (1988)]. Methods commonly employed to determine identity or homology between sequences include, but are not limited to, those disclosed in Guide to Huge Computers, Martin J. Bishop, ed., Academic Press, San Diego, 1994, and H. Carillo and D. Lipton, SIAM J. Applied Math., 48:1073 (1988). Preferred methods to determine identity or homology are designed to give the largest match between the two sequences tested. Methods to determine identity and similarity are codified in computer programs. Preferred computer program methods to determine identity and homology between two sequences include, but are not limited to, the algorithm BESTFIT from the GCG program package [J. Devereux et al., Nucl. Acids Res., 12(1):387 (1984)], the related MACVECTOR program (Oxford), and the FASTA (Pearson) programs, which may be used at default settings or modified setting such as determined to be suitable by one of skill in the art.

The p20 peptide or protein of the present invention may also be modified to increase its immunogenicity. For example, the antigen may be coupled to chemical compounds or immunogenic carriers, provided that the coupling does not interfere with the desired biological activity of either the antigen or the carrier. For a review of some general considerations in coupling strategies, see Antibodies, A Laboratory Manual, Cold Spring Harbor Laboratory, ed. E. Harlow and D. Lane (1988). Useful immunogenic carriers known in the art, include, without limitation, keyhole limpet hemocyanin (KLH), bovine serum albumin (BSA), ovalbumin, PPD (purified protein derivative of tuberculin), red blood cells, tetanus toxoid, cholera toxoid, agarose beads, activated carbon or bentonite. Useful chemical compounds for coupling include, without limitation, dinitrophenol groups and arsonilic acid.

The p20 peptides and proteins of the invention may also be modified by other techniques, such as by denaturation with heat and/or SDS. Alternatively, the peptides and proteins of the invention may be modified to provide an additional N- or C-terminal amino acid sequence suitable for biotinylation, e.g., cysteine or lysine.

A protein composition which may be a preferred alternative to the fusion proteins described above is a cocktail (i.e., a simple mixture) comprising a p20 peptide or protein.

In still another aspect, the peptide and proteins of the invention may be provided with a detectable label as described in detail below.

A peptide or protein antigen of the present invention may also be used in the form of a pharmaceutically acceptable salt. Suitable acids and bases which are capable of forming salts with the polypeptides of the present invention are well known to those of skill in the art and include inorganic and organic acids and bases.

The following examples illustrate the preferred methods for obtaining protein antigens of the invention and preparing the assays and compositions of the invention. Significantly, these examples indicate that the p20 peptides and proteins of this invention are useful for diagnosis of canine Lyme disease and contemplate prophylaxis against Lyme disease and may improve Lyme serology. These examples are illustrative only and do not limit the scope of the invention.

EXEMPLIFICATION

Materials And Methods

Spirochetes. *B. burgdorferi* 297 is a pathogenic sensu stricto isolate originally recovered from human spinal fluid (LeFebvre, R. B., G. C. Perng, and R. C. Johnson. 1989. Characterization of *Borrelia burgdorferi* isolates by restriction endonuclease analysis and DNA hybridization. J. Clin. Microbiol. 27:636-639). The spirochete contains ospA, ospB, and ospC, and expresses each when cultured at 35° C.

Animals. Fifteen-week-old laboratory purpose-bred beagle puppies were obtained from Ridglan Farms (Mount Horeb, Wis.) and housed individually at ambient temperature (21° C.). Food and water were provided ad libitum.

Ticks. Adult *I. scapularis* ticks were collected by flagging the underbrush in wooded areas in an endemic focus of *B. burgdorferi* infection located near Ettrick, Wis. (Jackson, C. A., S. D. Lovrich, W. A. Agger, and S. M. Callister. 2002. Reassessment of a Midwestern Lyme disease focus for *Borrelia burgdorferi* and the human granulocytic ehrlichiosis agent. J. Clin. Microbiol. 40:2070-2073.1). Ticks were transported immediately to the laboratory and stored at 8° C. in 95% humidity until used.

Challenge and confirmation of infection. Dogs were shaved on the right side of the thoracic cavity, and each dog was challenged with 10 female and 10 male *I. scapularis* ticks that were placed in a rubber cup and secured to the shaved area with bandage wrap and tape. The ticks were allowed to feed for 7 days. Skin biopsies were collected at approximately one and three months after the tick-challenge by injecting a site near the bite sites with 0.5 ml of lidocaine (2%) and removing a biopsy with a disposable 4 mm puncture device. The biopsies were placed immediately into separate tubes containing 9 ml of Barbour-Stoenner-Kelly (BSK) medium supplemented with gelatin (20%) and the antibiotics rifampin (40 µg/ml) and kanamycin (8 µg/ml). The cultures were vortexed and a one ml-amount was transferred to an additional tube that also contained 9 ml of BSK (ten-fold dilution). The original and diluted cultures were then incubated at 35° C. and examined weekly for 4 weeks. The ability of the BSK to support growth from an inoculum of one organism (Callister, S. M., K. L. Case, W. A. Agger, R. F. Schell, R. C. Johnson, and J. L. E. Ellingson. 1990. Effects of bovine serum albumin on the ability of Barbour-Stoenner-Kelly medium to detect *Borrelia burgdorferi*. J. Clin. Microbiol. 28:363-365) was confirmed prior to culture.

Collection and processing of blood serum. Blood samples were also obtained at approximately one and three months post tick-challenge by venipuncture of the jugular vein. The serum was separated by centrifugation and stored at −20° C. until used.

Detection of C6 peptide antibodies. *B. burgdorferi* antibodies specific for the C6 peptide were detected by using a commercially-available test (SNAP® 4Dx®, IDEXX Laboratories, Westbrook, Me.) according to the manufacturer's directions.

Western blotting. Western blotting was performed using standard techniques. Briefly, *B. burgdorferi* 297 was boiled for 5 min and 225 mg of protein was loaded onto a 10% to 20% gradient polyacrylamide gel (Bio-Rad, Hercules, Calif.). After electrophoresis, the proteins were transferred to polyvinylidene fluoride (PVDF) membranes and blocked with 1% bovine serum albumin (BSA) in phosphate buffered saline-0.1% Tween 20 (PBS-T). Strips were then incubated with diluted serum (1:100) and washed with PBS-T. Horseradish peroxidase-labeled anti-dog IgM or IgG (Kirkegaard & Perry Laboratories, Gaithersburg, Md.) diluted 1:3,000 or 1:6,000, respectively, was then added, and the strips were developed with the TMB (3,3',5,5'-tetramethylbenzidine) Membrane Peroxidase Substrate System (Kirkegaard & Perry Laboratories).

Removal of OspC antibodies. Recombinant (r) OspC7 was recovered from *E. coli* JM109 containing pX3-22 and bound to Tetralink tetrameric avidin resin (Promega, Madison, Wis.) contained within a column as described previously (Jobe, D. A., S. D. Lovrich, R. F. Schell, and S. M. Callister. 2003. C-terminal region of outer surface protein C binds borreliacidal antibodies in sera from patients with Lyme disease. Clin. Diagn. Lab. Immunol. 10:573-578; Rousselle, J. C., S. M. Callister, R. F. Schell, S. D. Lovrich, D. A. Jobe, J. A. Marks, and C. A. Wieneke. 1998. Borreliacidal antibody production against outer surface protein C of *Borrelia burgdorferi*. J. Infect. Dis. 178:733-741). One-ml volumes of immune serum diluted ten-fold in PBS were passed over the columns four times.

Results

Transmission of *B. burgdorferi* by infected ticks. After the tick challenge, *B. burgdorferi* were recovered from at least one skin biopsy from 24 (80%) dogs (Table 1).

Figure 1:
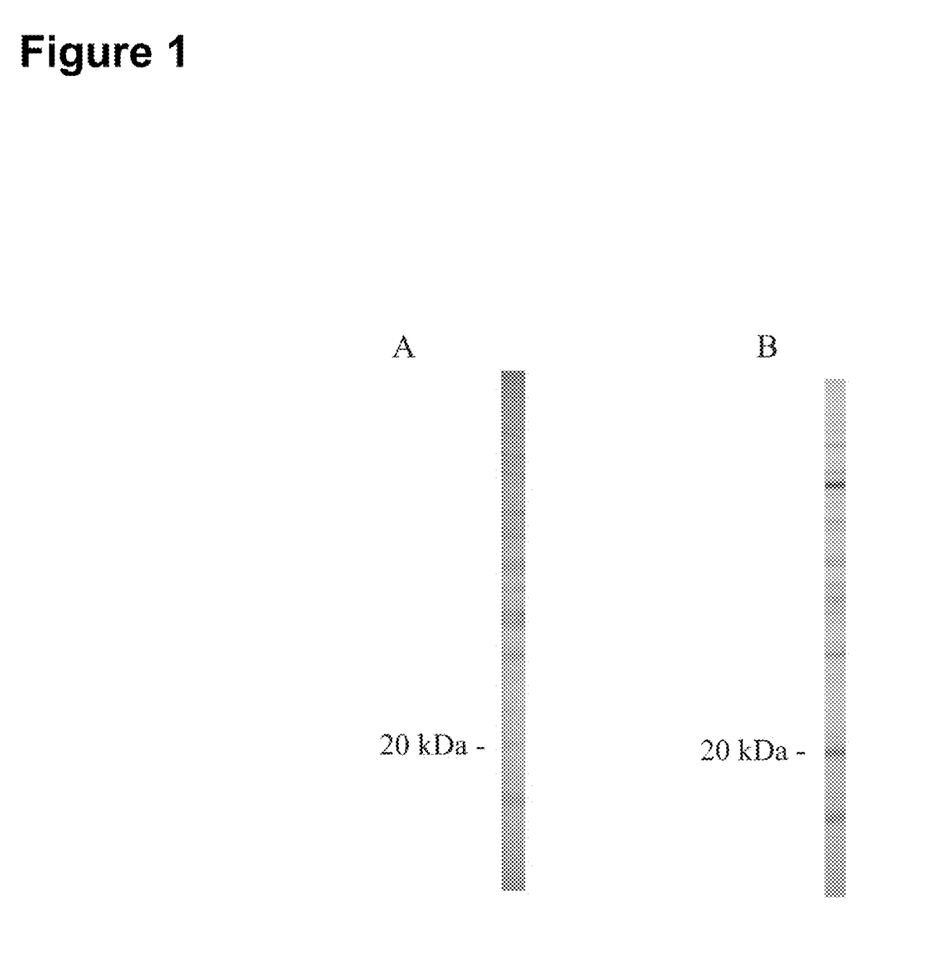

Antibody responses after infection. The dogs (n=6) with negative skin biopsy results also remained seronegative by Western blotting, so the animals were likely not infected with *B. burgdorferi* by the tick challenge and the sera were not evaluated further. In contrast, the immune sera collected from the 24 dogs with positive skin biopsies after approximately one month contained immunoglobulin (Ig)M (FIG. 1A) and IgG (FIG. 1B) antibodies, and the banding patterns of the IgG antibodies were identical to the patterns reported previously (Lovrich, S. D., R. L. LaFleur, D. A. Jobe, J. C. Johnson, K. E. Asp, R. F. Schell, and S. M. Callister. 2007. Borreliacidal OspC antibody response of canines with Lyme disease differs significantly from that of humans with Lyme disease. Clin. Vacc. Immunol. 14:635-637). In addition, IgM and IgG antibodies specific for the approximately 20 kDa protein were detected in 3 (21%) sera and 18 (75%) sera, respectively (Table 2). Moreover, the IgG 20 kDa antibodies in each positive immune sera remained detectable after 3 months, and the response expanded to include three additional dogs (n=21, 88%). In contrast, antibodies specific for the C6 peptide were detected in only 3 (13%, p>0.0001) immune sera collected one month after tick-challenge, and the response was detected 16 (67%) sera after three months (Table 3). Additionally, each immune serum that contained C6-specific antibodies also contained 20 kDa protein antibodies.

TABLE 1

Recovery of spirochetes from skin biopsies obtained from dogs challenged with *B. burgdorferi*-infected *Ixodes scapularis* ticks.

| | Detection (+/−) of *B. burgdorferi* in skin biopsies obtained after: | |
|---|---|---|
| Dog (no.) | 1 month[a] | 3 months[b] |
| 1 | + | − |
| 2 | + | + |
| 3 | + | + |
| 4 | + | + |
| 5 | − | + |
| 6 | + | − |
| 7 | − | + |
| 8 | + | + |
| 9 | + | + |
| 10 | + | + |
| 11 | + | + |
| 12 | + | + |
| 13 | + | + |
| 14 | + | − |
| 15 | + | + |
| 16 | − | + |
| 17 | + | − |
| 18 | + | + |
| 19 | + | + |
| 20 | + | + |
| 21 | + | + |
| 22 | + | − |
| 23 | + | − |
| 24 | + | + |
| 25 | − | − |
| 26 | − | − |
| 27 | − | − |
| 28 | − | − |
| 29 | − | − |
| 30 | − | − |
| Total | 21 (70%) | 18 (60%) |

[a]Collected 36-43 days post tick-challenge.
[b]Collected 92-112 days post tick-challenge.

TABLE 2

Detection of 20 kDa antibodies in sera from dogs challenged with *B. burgdorferi*-infected *Ixodes scapularis* ticks.

| | Detection (+/−) of 20 kDa protein antibodies by Western blot after: | | |
|---|---|---|---|
| Dog | 1 month[a] | | 3 months[b,c] |
| (no.) | IgM | IgG | IgG |
| 1 | − | + | + |
| 2 | − | + | + |
| 3 | − | + | + |
| 4 | − | + | + |
| 5 | − | − | + |
| 6 | − | − | + |
| 7 | − | + | + |
| 8 | − | + | + |
| 9 | − | + | + |
| 10 | − | + | + |
| 11 | − | + | + |
| 12 | + | + | + |
| 13 | + | + | + |
| 14 | − | + | + |
| 15 | − | + | + |
| 16 | − | − | − |
| 17 | − | − | − |
| 18 | − | + | + |
| 19 | − | + | + |
| 20 | + | + | + |
| 21 | − | + | + |
| 22 | − | + | + |
| 23 | − | − | − |
| 24 | − | − | + |
| Total | 3 (13%) | 18 (75%) | 21 (88%) |

[a]Collected 36-43 days post tick-challenge.
[b]Collected 92-112 days post tick-challenge.
[c]IgM antibodies not evaluated.

TABLE 3

Detection of C6 antibodies in sera from dogs challenged with
B. burgdorferi-infected Ixodes scapularis ticks.

| | Detection (+/−) of C6 peptide antibodies after: | |
|---|---|---|
| Dog (no.) | 1 month[a] | 3 months[b] |
| 1 | − | + |
| 2 | − | + |
| 3 | − | − |
| 4 | − | + |
| 5 | − | − |
| 6 | − | + |
| 7 | − | + |
| 8 | − | + |
| 9 | + | + |
| 10 | − | + |
| 11 | − | + |
| 12 | − | + |
| 13 | − | + |
| 14 | − | − |
| 15 | − | − |
| 16 | − | − |
| 17 | − | − |
| 18 | − | − |
| 19 | − | + |
| 20 | + | + |
| 21 | − | + |
| 22 | + | + |
| 23 | − | − |
| 24 | − | + |
| Total | 3 (13%) | 16 (67%) |

[a]Collected 36-43 days post tick-challenge.
[b]Collected 92-112 days post tick-challenge.

Figure 2:
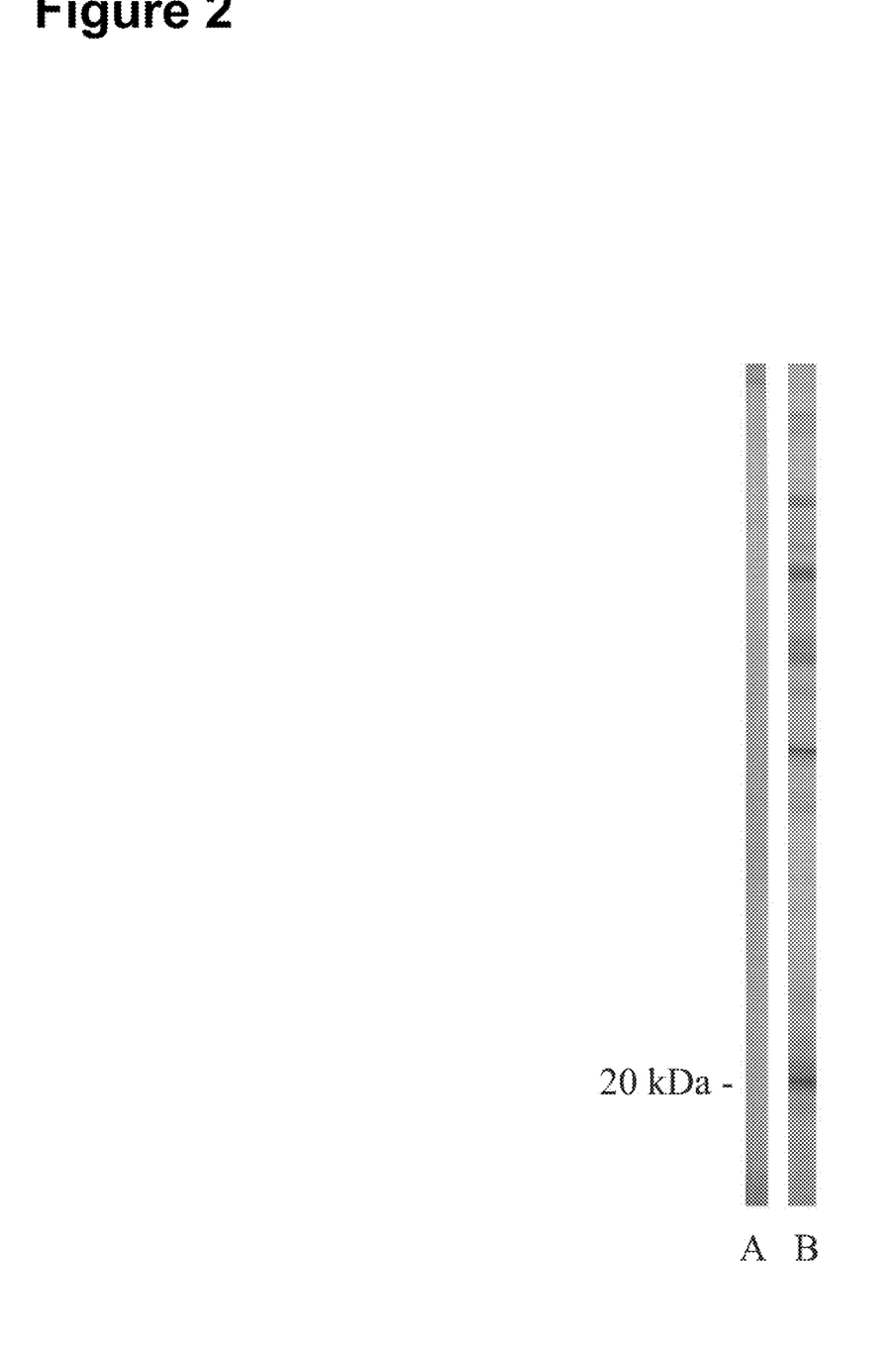

Effect of removing OspC antibodies on 20 kDa protein antibodies. Well-described OspC antibodies (Wieneke, C. A., S. D. Lovrich, S. M. Callister, D. A. Jobe, J. A. Marks, and R. F. Schell. 2000. Evaluation of whole-cell and OspC enzyme-linked immunosorbent assays for discrimination of early Lyme borreliosis from OspA vaccination. J. Clin. Microbiol. 38:313-317) are also induced in vivo by an approximately 20 kDa B. burgdorferi protein. We therefore passed the anti-20 kDa antibody-positive immune sera over a column that contained rOspC (recombinant OspC) to remove OspC-specific antibodies, and then examined the effect on the anti-20 kDa protein canine antibodies detected by Western blot. The immune sera commonly contained small concentrations of OspC antibodies that could be detected by the OspC ELISA, but the antibodies were removed completely after passage over the column (data not shown). More significantly, the anti-20 kDa protein antibodies specific for canine infection with B. burgdorferi were not affected (FIG. 2).

Lack of Detection of 20 kDa Antibodies after Vaccination. Dogs vaccinated for B. burgdorferi with a whole cell Lyme disease bacterin were also screened for the presence of antibodies to the p20 kDa peptide. Additionally, dogs subjected to tick challenge were also screened for the presence of antibodies to the p20 kDa peptide.

Fifteen laboratory-bred beagle dogs were vaccinated with a commercial vaccine comprising whole cell bacterin as prescribed by the manufacturer. The whole cell bacterin was comprised of two isolates. B. burgdorferi S-1-10, a pathogenic sensu stricto isolate recovered from the kidney of a white-footed mouse captured near La Crosse, Wis. that is currently incorporated into a commercially available Lyme disease vaccine (Galaxy Lyme), and B. burgdorferi 50772, a unique noninfectious ospA- and ospB-negative sensu stricto isolate (La Fleur, R L, J C Dant, T L Wasmoen, S M Callister, D A Jobe, S D Lovrich, T F Warner, O Abdelmagid and RF Schell. 2009. Bacterin that induces anti-OspA and anti-OspC borreliacidal antibodies provides a high level of protection against canine Lyme disease. Clin Vacc Immunol (doi: 10.1128/CVI.00373-08: epublished Dec. 3, 2008).

As briefly described in the example above, healthy non-vaccinated laboratory-bred beagle dogs were challenged and infection was confirmed as follows. To ensure that the animals were not exposed to B. burgdorferi previously, serum samples were obtained prior to the study, and seronegativity was confirmed by using a B. burgdorferi 297 whole-cell ELISA (Wieneke, C. A., et al. 2000. Evaluation of whole-cell and OspC enzyme-linked immunosorbent assays for discrimination of early Lyme borreliosis from OspA vaccination. J. Clin. Microbiol. 38:313-317). Ticks were collected from a focus of endemicity near La Crosse, Wis. (Jackson, C. A., et al., 2002. Reassessment of a Midwestern Lyme disease focus for Borrelia burgdorferi and the human granulocytic ehrlichiosis agent. J. Clin. Microbiol. 40:2070-2073) and infection was confirmed by examining the midguts from 100 adult male ticks after staining with fluorescein isothiocyanate-labeled OspA monoclonal antibody H5332 (ibid.). B. burgdorferi was detected in 30 (30%) ticks. Infected ticks were placed into a rubber cup that was secured to the left dorsal-anterior region of each animal for 1 week. The dogs were isolated, fed commercial food and water ad libitum and observed daily for lameness.

To confirm transmission of spirochetes by the tick challenge, 4-mm-punch skin biopsies were obtained from the tick bite sites at 30 and 90 days post-challenge (1 and 3 months), placed into separate tubes containing 9 ml of modified Barbour-Stoenner-Kelly medium (Callister, S. M., et al., 1990. Effects of bovine serum albumin on the ability of Barbour-Stoenner-Kelly medium to detect Borrelia burgdorferi. J. Clin. Microbiol. 28:363-365), incubated at 34° C. and examined weekly by dark-field microscopy. Vaccinated dogs were vaccinated with a commercial vaccine comprising whole cell bacterin as prescribed by the manufacturer.

Table 4, below, shows that dogs previously vaccinated were not positive for antibodies specific for the p20 kDa peptide whereas tick challenged unvaccinated dogs tested positive at 1 and 3 months.

TABLE 4

Sensitivity of 20 kDa antibodies

| | Number (%) 20 kDa positive after: | |
|---|---|---|
| Sample (no.) | 1 month | 3 months |
| vaccinated[a] (15) | 0 | 0 |
| infected dogs[b]* (24) | 18 (75) | 21 (88) |

[a]whole cell bacterin
[b]positive skin biopsy
*data from non-vaccinated dogs is from the Table 2 above.

Conclusions 20 kDa protein antibodies were NOT OspC-specific.

IgM 20 kDa protein antibodies were only rarely present after one month—which suggests they are only rarely produced and IgG antibodies predominate or the class-switch from IgM to IgG antibodies occurred quickly.

Significant levels of IgG 20 kDa protein antibodies were produced rapidly (within one month) after B. burgdorferi infection.

Confirmation of Lyme disease by detection of 20 kDa protein antibodies was significantly (p>0.0001) more sensitive than confirmation by detection of C6 antibodies (current gold standard) during early canine Lyme disease.

The 20 kDa protein antibodies were not induced by vaccination and not affected by previous vaccination.

The invention claimed is:

1. A method of distinguishing vaccinated or non-vaccinated animals that have been infected with *Borrelia burgdorferi* from a) non-vaccinated animals that have not been infected with *Borrelia burgdorferi* and b) animals that have been vaccinated with a *Borrelia burgdorferi* vaccine that does not stimulate substantial production of an antibody reactive with a 20 kDa polypeptide in a Western blot assay, but have not been infected with *Borrelia burgdorferi*, the method comprising:
   a) contacting a biological sample from an animal with an isolated *Borrelia burgdorferi* polypeptide with an apparent molecular weight of 20 kDa, wherein the polypeptide specifically binds to antibodies that are a component of the animal's immune response to a *Borrelia burgdorferi* infection; and
   b) detecting whether antibodies in the sample specifically bind to the *Borrelia burgdorferi* polypeptide;
   wherein, if antibodies in the biological sample specifically bind to the polypeptide, then the animal is infected with *Borrelia burgdorferi* and is distinguished from a) non-vaccinated animals that have not been infected with *Borrelia burgdorferi* and b) animals that have been vaccinated with a *Borrelia burgdorferi* vaccine that does not stimulate substantial production of an antibody reactive with a 20 kDa polypeptide in a Western blot assay, but have not been infected with *Borrelia burgdorferi*.

2. A method of distinguishing vaccinated and non-vaccinated animals that have been infected with *Borrelia burgdorferi* from a) animals that have been vaccinated with a *Borrelia burgdorferi* vaccine that does not stimulate substantial production of an antibody reactive with a 20 kDa polypeptide in a Western blot assay, but have not been infected with *Borrelia burgdorferi* and b) animals that have not been infected with *Borrelia burgdorferi*, the method comprising:
   a) providing a biological sample from the animal; and
   b) determining whether the sample contains antibodies capable of specifically binding an isolated *Borrelia burgdorferi* polypeptide with an apparent molecular weight of 20 kDa, wherein the antibodies are a component of the animal's immune response to an *Borrelia burgdorferi* infection;
   wherein if the sample contains antibodies capable of specifically binding the 20 kDa polypeptide, then the animal has been infected with *Borrelia burgdorferi*; and is distinguished from a) animals that have been vaccinated with a *Borrelia burgdorferi* vaccine that does not stimulate substantial production of an antibody reactive with a 20 kDa polypeptide in a Western blot assay, but have not been infected with *Borrelia burgdorferi* and b) animals that have not been infected with *Borrelia burgdorferi*.

3. The method of claim 1 or 2, wherein the polypeptide does not specifically bind to antibodies that are a component of the animal's immune response to a vaccination for *Borrelia burgdorferi*.

4. The method of claim 3, wherein said vaccination comprises inactivated *Borrelia burgdorferi* cells.

5. The method of claim 1 or 2, wherein the biological sample is selected from a group consisting of blood and serum.

6. The method of claim 1 or 2, wherein antibodies reactive with the polypeptide with an apparent molecular weight of 20 kDa are detected as early as 1 month post-infection.

7. The method of claim 1 or 2, wherein the antibodies reactive with the polypeptide with an apparent molecular weight of 20 kDa are detected before the onset of clinical symptoms.

8. The method of claim 1 or 2, wherein the animal is a canine.

* * * * *